United States Patent [19]

Tokuyama et al.

[11] Patent Number: 5,525,501

[45] Date of Patent: Jun. 11, 1996

[54] DNA FRAGMENT ENCODING ACYLAMINO ACID RACEMASE

[75] Inventors: Masaharu Tokuyama, Kobe; Kazunori Hatano, Kawanishi; Kazuo Nakahama, Nagaokakyo; Takeshi Takahashi, Izumi, all of Japan

[73] Assignee: Takeda Chemical Industries, Ltd., Osaka, Japan

[21] Appl. No.: 347,221

[22] Filed: Nov. 23, 1994

Related U.S. Application Data

[63] Continuation of Ser. No. 984,310, Dec. 1, 1992, abandoned, which is a continuation-in-part of Ser. No. 668,475, Mar. 13, 1991, abandoned.

[30] Foreign Application Priority Data

Sep. 14, 1990 [JP] Japan .................................. 2-245257

[51] Int. Cl.⁶ ........................... C12N 9/90; C12N 15/61; C12N 1/21; C12N 15/63
[52] U.S. Cl. ..................... 435/233; 435/69.1; 435/252.3; 435/320.1; 435/826; 536/23.2; 536/23.7
[58] Field of Search .................................. 536/23.2, 23.7; 435/320.1, 233, 252.3, 826, 69.1

[56] References Cited

U.S. PATENT DOCUMENTS

| | | | |
|---|---|---|---|
| 4,335,209 | 6/1982 | Asai et al. | 435/108 |
| 4,906,572 | 3/1990 | Shimazu et al. | 435/233 |
| 4,981,799 | 1/1991 | Takahashi et al. | 435/233 |

FOREIGN PATENT DOCUMENTS 304021   2/1989   European Pat. Off. .

OTHER PUBLICATIONS

Soda et al., Crystalline Amino Acid Racemase . . . , *Biochem. and Biophy. Res. Comm.* 35:363–368, 1969.

Nakajima et al., Cloning and Expression in *E. Coli* of the Glutamate Racemase Gene . . . , *Agric, Biol, Chem.* 50:2823–2830, 1986.

Chemical Abstracts, vol. 111, No. 21, Nov. 20, 1989, Columbus, Ohio, US; Abstract No. 188773.

Chemical Abstracts, vol. 107, No. 7, Aug. 17, 1987, Columbus, Ohio US; Abstract No. 53505c.

Katz et al., "Cloning and Expression of the Tyrosinase Gene from *Streptomyces antibioticus* in *Streptomyces lividans*", Journal of General Microbiology, 129, pp. 2703–2714, 1993.

Seno et al., "The Glycerol Utilization Operon of *Streptomyces coelicolor;* Genetic Mapping of gyl Mutations and the Analysis of Cloned gyl DNA", Molecular General Genetics, 193, pp. 119–128, 1984.

Ikeda et al., "Genetic mapping, cloning and physiological aspects of the glucose kinase gene of *Streptomyces coelicolor*", Molecular General Genetics, 196, pp. 501–507, 1994.

Feitelson et al., "Cloning of a *Streptomyces* Gene for an O–Methyltransferase Involved in Antibiotic Biosynthesis", Molecular General Genetics, 190, pp. 394–398, 1983.

Burnett et al., "Cloning and Analysis of an Exported β–Galactosidase and other Proteins from *Streptomyces lividans*", Microbiology–1985 (Ed. L. Leive), pp. 441–444.

Leive, "Cloning and Analysis of an Exported β–Galactosidase and other Proteins lividans", Microbiology–1985, pp. 441–448.

*Primary Examiner*—Stephen G. Walsh
*Attorney, Agent, or Firm*—Wenderoth, Lind & Ponack

[57] ABSTRACT

The present invention relates to a DNA fragment containing a gene encoding acylamino acid racemase. The acylamino acid racemase can be produced industrially at high efficiency using the DNA fragment.

10 Claims, 9 Drawing Sheets

FIG. 1(A)

```
GAATTCCCCG GGTGACCGGC TTCGACCGAG CCGGCTTTTA CGTGATCTCC AAGGAGGAGC    60
A GTG AAA CTC AGC GGT GTG GAA CTG CGC CGG GTG CAG ATG CCG CTC GTC   109
  Met Lys Leu Ser Gly Val Glu Leu Arg Arg Val Gln Met Pro Leu Val
   1           5                  10                  15

GCC CCG TTC CGG ACT TCG TTC GGC ACC CAG TCG GTC CGC GAG CTC TTG    157
Ala Pro Phe Arg Thr Ser Phe Gly Thr Gln Ser Val Arg Glu Leu Leu
            20                  25                  30

CTG CTG CGC GCG GTC ACG GCG CCG GCC GGC GAG GGC TGG GAA TGC GTG    205
Leu Leu Arg Ala Val Thr Ala Pro Ala Gly Glu Gly Trp Glu Cys Val
 35                  40                  45

ACG ATG GCC GGT CCG CTG TAC TCG GAG TCG TAC AAC GAC GGC GCG GAA    253
Thr Met Ala Gly Pro Leu Tyr Ser Glu Ser Tyr Asn Asp Gly Ala Glu
         50                  55                  60

CAC GTG CTG CGG CAC TAC TTG ATC CCG GCG CTG CTG GCC GCG GAA GAC    301
His Val Leu Arg His Tyr Leu Ile Pro Ala Leu Leu Ala Ala Glu Asp
 65                  70                  75                  80

ATC ACC GCG AAG GTG GCG AAG TTG GCC CTG CTG CCG CTC GCC GAA CAC    349
Ile Thr Ala Lys Val Ala Lys Leu Ala Leu Leu Pro Leu Ala Glu His
             85                  90                  95

CGG ATG GCC AAG GCC GCG CTG GAG ATG GCC GTG CTC GAC GCC GAA CTC    397
Arg Met Ala Lys Ala Gly Ala Leu Glu Met Ala Val Leu Asp Ala Leu
                100                 105                 110

CGC GCG CAC GAG AGG TCG TTC GCC GCG GAA CTC GGA TCG GTG CGC GAT    445
Arg Ala His Glu Arg Ser Phe Ala Ala Glu Leu Gly Ser Val Arg Asp
            115                 120                 125

TCT GTG CCG TGC GGC GTT TCG GTC GGG ATC ATG GAC ACC ATC CCG CAA    493
Ser Val Pro Cys Gly Val Ser Val Gly Ile Met Asp Thr Ile Pro Gln
                130                 135                 140

CTC CTC GAC GTC GTG GGC GGA TAC CTC GAC GAG GGT TAC GTG CGG ATC    541
Leu Leu Asp Val Val Gly Gly Tyr Leu Asp Glu Gly Tyr Val Arg Ile
145                 150                 155                 160
```

FIG. 1(B)

```
AAG CTG AAG ATC GAA CCC GGC TGG GAC GTC GAG CCG GTG CGC GCG GTC    589
Lys Leu Lys Ile Glu Pro Gly Trp Asp Val Glu Pro Val Arg Ala Val
                165                 170                 175

CGC GAG CGC TTC GGC GAC GTG CTG CAG GTC GAC GCG AAC ACC            637
Arg Glu Arg Phe Gly Asp Val Leu Leu Gln Val Asp Ala Asn Thr
            180                 185                 190

GCC TAC ACC CTC GGC GAC GCG CCG CAG CTG GCC CGG CTC GAC CCG TTC    685
Ala Tyr Thr Leu Gly Asp Ala Pro Gln Leu Ala Arg Leu Asp Pro Phe
                195                 200                 205

GGC CTG CTG CTG ATC CTG GAG CAG CCG CTG GAA GAG GAC GTG CTC GGC    733
Gly Leu Leu Leu Ile Leu Glu Gln Pro Leu Glu Glu Asp Val Leu Gly
                210                 215                 220

CAC GCC GAA CTG GCC CGG ATC CAG ACA CCG ATC TGC CTC GAC GAG        781
His Ala Glu Leu Ala Arg Ile Gln Thr Pro Ile Cys Leu Asp Glu
        225                 230                 235             240

TCG ATC GTG TCG GCG GCG GCG GAC GCC AAG ATC CTG GGC GCG            829
Ser Ile Val Ser Ala Arg Ala Ala Asp Ala Lys Ile Leu Gly Ala
                245                 250                 255

GTC CAA ATC GTG AAC ATC AAA CCG GGC GTC CGC GGG TAC CTG GAA        877
Val Gln Ile Val Asn Ile Lys Pro Gly Arg Val Gly Gly Tyr Leu Glu
                260                 265                 270

GCG CGG CGG GTG CAC GAC GTG TGC GCG GCG CAC GGG ATC CCG GTG TGG    925
Ala Arg Arg Val His Asp Val Cys Ala Ala His Gly Ile Pro Val Trp
                275                 280                 285

TGC GGG GGG ATG ATC GAG ACC GGC CTC GGC CGG GCG GCG AAC GTC GCG    973
Cys Gly Gly Met Ile Glu Thr Gly Leu Gly Arg Ala Ala Asn Val Ala
                290                 295                 300

CTG GCC TCG CTG CCC AAC TTC ACC CTG CCC GGC GAC ACC TCG GCG TCG   1021
Leu Ala Ser Leu Pro Asn Phe Thr Leu Pro Gly Asp Thr Ser Ala Ser
        305                 310                 315             320
```

FIG. 1(C)

```
GAC CGG TTC TAC AAA ACC GAC ATC ACC GAG CCG TTC GTG CTC TCC GGC      1069
Asp Arg Phe Tyr Lys Thr Asp Ile Thr Glu Pro Phe Val Leu Ser Gly
                325                 330                 335

GGC CAC CTC CCG GTG CCG ACC GGA CCG GGC GTG CTC GGC GTG GCG CCG ATT  1117
Gly His Leu Pro Val Pro Thr Gly Pro Gly Val Leu Gly Val Ala Pro Ile
            340                 345                 350

CCG GAG CTG CTG GAC GAG GTG ACC ACG GCA AAG GTG TGG ATC GGT TCG      1165
Pro Glu Leu Leu Asp Glu Val Thr Thr Ala Lys Val Trp Ile Gly Ser
                355                 360                 365

TAGCCCGCTA CGAATTCCGG AGGTAGATTT GGTCGGATCG GACCAGCCGG TCCGCACGAG    1225
GCCGGATCTA CCTTCGGGGG GTGCTGACAC CGGTGCCGAG CAAACCCGAC ACGAGTCTGG    1285
GACGCGTCCT CGAAGCTCTC GGGGACGTGC TCCTCGAGCC GGTCGCCGTC GGCGCGACAC    1345
GCGGGGGCAG CTCGGGCGGG TGGTGATTCA CGACCCGCAC GACGACGCGG AATTC         1400
```

DNA FRAGMENT ENCODING ACYLAMINO ACID RACEMASE

This application is a continuation of now abandoned application Ser. No. 07/984,310 filed Dec. 1, 1992 which was a continuation-in-part of now abandoned application Ser. No. 07/668,475 filed Mar. 13, 1991.

FIELD OF THE INVENTION

This invention relates to a fermentative method of producing acylamino acid racemase, to a novel microorganism useful in said method and to a novel DNA fragment useful in producing said novel microorganism.

BACKGROUND OF THE INVENTION

Acylamino acid racemase is widely distributed among actinomycetes. It is a specific enzyme which catalyzes the racemization of optically active N-acylamino acids but does not act on optically active amino acids, and its properties have already been made clear in detail (U.S. Pat. No. 4,981,799; Abstracts of Papers presented at the 1990 Annual Meeting of the Japan Society for Bioscience, Biotechnology, and Agrochemistry, page 368, 1990).

As mentioned above, acylamino acid racemase is a useful enzyme utilizable in the production of optically active amino acids. However, any satisfactory process for producing said enzyme at low cost and in an efficient manner has not been developed as yet and, accordingly, the advent of a more advantageous method has been awaited.

Under these circumstances, the present inventors made intensive investigations and made a report on acylamino acid racemase produced by Amycolatopsis sp. TS-1-60 (Abstracts of Papers presented at the 1990 Annual Meeting of the Japan Society for Bioscience, Biotechnology, and Agrochemistry, page 368, 1990). Furthermore they succeeded in cloning a DNA encoding said acylamino acid racemase from Amycolatopsis sp. TS-1-60 and, after further investigations, they have now completed the present invention.

SUMMARY OF THE INVENTION

The present invention provides a DNA fragment containing a gene encoding acylamino acid racemase, a vector with said DNA fragment inserted therein, a novel microorganism transformed with said vector and capable of producing acylamino acid racemase, and a method of producing acylamino acid racemase which comprises using said microorganism.

BRIEF DESCRIPTION OF THE DRAWINGS

FIG. 1 shows the base sequence of a gene encoding acylamino acid racemase as determined in Example 3 (SEQ ID NO: 1).

DETAILED DESCRIPTION OF THE PREFERRED EMBODIMENT

Figure 2:
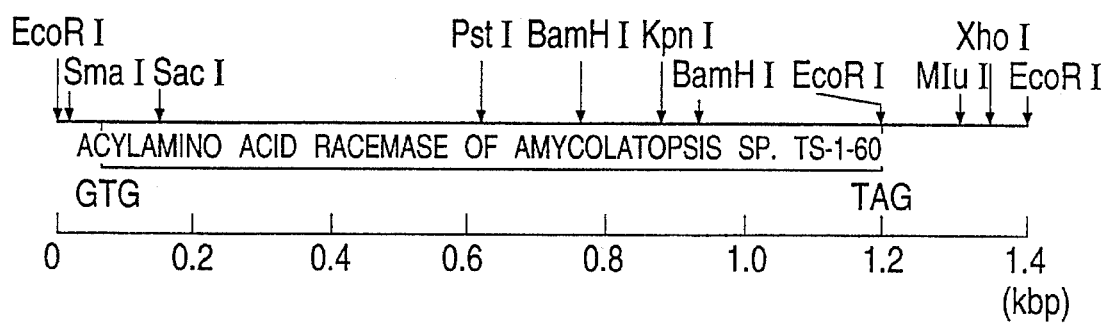
FIG. 2 shows a restriction enzyme cleavage map of the DNA fragment containing the gene encoding acylamino acid racemase obtained in Example 1.

The DNA fragment according to the invention which contains a gene encoding acylamino acid racemase (hereinafter sometimes referred to also as acylamino acid racemase-encoding DNA or simply as acylamino acid racemase DNA) has been discovered for the first time by the present inventors and can be produced by isolating the relevant DNA from the acylamino acid racemase producing actinomycetes, for example, Streptomyces sp. Y-53 (IFO 14596; FERM P-9518) or Amycolatopsis sp. TS-1-60 (IFO 15079; FERM BP-3092) and others, inserting said DNA into a phage or plasmid, transforming a host with the resulting recombinant phage or plasmid, cultivating the transformants obtained, isolating a phage or plasmid containing the desired DNA from among the transformants by an appropriate method, for example by immunoassay using an acylamino acid racemase antibody or by plaque or colony hybridization using a DNA probe, excising the desired cloned DNA from the phage or plasmid and subcloning said cloned DNA into an appropriate plasmid. The thus-obtained DNA can be inserted into a plasmid or phage and the resulting recombinant can be used for the transformation of a host, for example *Escherichia coli*, an actinomycete or a yeast.

The IFO numbers given above denote the deposit numbers at the Institute for Fermentation, Osaka (IFO) and the FERM P or FERM BP numbers denote the deposit numbers at the Fermentation Research Institute (FRI), Agency of Industrial Science and Technology, Ministry of International Trade and Industry; the same shall apply hereinafter.

Typical mycological properties of Amycolatopsis sp. TS-1-60 are shown below.

(a) Morphology

After shaking at 28° C. for 24 to 48 hours in a nutrient liquid medium [e.g. Trypticase Soy Broth, (Becton Dickinsor)], the substrate mycelia divide into small fragments resembling rod bacteria or branched short lengths of hyphae.

The substrate mycelium on agar medium shows zigzag forms. The aerial mycelium usually exhibits straight or flexuous (Rectus Flexibilis).

acoremium is observed on agar media ISP-2 and ISP-7. The spore shows a cylindrical form (0.3 to 0.5×0.6 to 2.3 μm) with smooth surfaces.

(b) Cultural characteristics

Cultural characteristics of TS-1-60 strain on various media are shown in Table 2. Colors represented in Table 1 are determined by comparing them with color chips of the "Color Harmony Manual", 4th edition, Container Corporation of America.

TABLE 1

Cultural characteristics of strain TS-1-60 on Various Media

| Medium | Growth | Color of Aerial Mycelium | Color of substrate mycelium (reverse Color) | Soluble pigment |
|---|---|---|---|---|
| Sucrose nitrate agar | Poor | Scant, white | Lt Ivory(2ca) | None |
| Glucose-asparagine agar | Abundant, flat | Moderate, white | Lt Ivory(2ca) to Pearl Pink(3ca) | None |
| Glycerol-asparagine agar | Abundant, wrinkled | Abundant, cottony white | Lt Wheat(2ea) | None |
| Inorganic salts-starch agar (ISP medium 4) | Poor | Scant, white | Colorless to Lt Ivory(2ca) | None |
| Tyrosine agar (ISP medium 7) | Abundant | Abundant, cottony white | Lt Wheat(2ea) | Faint yellow |
| Nutrient agar | Moderate | None | Lt Ivory(2ca) | None |
| Yeast extract-malt extract agar (ISP medium 2) | Abundant, wrinkled, raised up with crack | Moderate, white | Honey Gold(2ic) | Faint yellow |
| Oatmeal agar (ISP medium 3) | Moderate, flat | Poor, white | Lt Ivory(2ca) to Lt Wheat(2ea) | None |

(c) Physiological characteristics

| | |
|---|---|
| Formation of melanin pigment | Negative |
| Coagulation of milk | Negative |
| Peptonization of milk | Negative |
| Liquefaction of gelatin | Negative |
| Hydrolysis of starch | Negative |
| NaCl tolerance (%) | 5< >7 |
| Temperature range for growth (°C.) | 13–37 |
| Optimum temperature for growth (°C.) | 20–30 |
| Temperature for no growth (°C.) | 40 |

(d) Utilization of carbon source

Positive: L-Arabinose, D-Xylose, D-Glucose, D-Fructose, Inositol, D-Mannitol

Negative: Sucrose, L-Rhamnose, Raffinose

As the plasmid suited for insertion of said DNA thereinto, there may be mentioned, among others, *Escherichia coli*-derived pBR322 [Gene, 2, 95 (1977)], pBR325 [Gene, 4, 121 (1978)] and pUC13 [Gene, 19, 259, (1982)]. Any other plasmid may also be used if it can be replicated and maintained in the host. As the phage vector for DNA insertion thereinto, there may be mentioned, for instance, λgt11 [Young, R. and Davis, R., Proc. Natl. Acad. Sci. U.S.A., 80, 1194 (1983)]. Other phage vectors may be used as well if they can multiply in the host.

As the method of inserting said DNA into a plasmid, there may be mentioned, for instance, the method described in Maniatis, T. et al., Molecular Cloning, Cold Spring Harbor Laboratory, page 239 (1982). Suited for DNA insertion into a phage vector is the method of Huynh, T. V. et al., DNA Cloning, a practical approach, 1, 49 (1985), for instance. the recombinant plasmid or phage vector thus obtained is introduced into an appropriate host, for example *Escherichia coli*.

As examples of said *Escherichia coli*, there may be mentioned, among others, *Escherichia coli* K12, DH1 [Proc. Natl. Acad. Sci. U.S.A., 60, 160 (1968)], JM103 [Nucl. Acids Res., 9, 309 (1981)], JA221 [J. Mol. Biol., 120, 517 (1978)], HB101 [J. Mol. Biol., 41, 459 (1969)] and C600 [Genetics, 39, 440 (1954)].

As the method of transforming a host with the plasmid, there may be mentioned, for instance, the calcium chloride method described in Maniatis, T. et al., Molecular Cloning, Cold Spring Harbor Laboratory, page 239 (1982), or the calcium chloride/rubidium chloride method. The phage vector can be introduced into grown *Escherichia coli*, for instance, by using the in vitro packaging technique.

An acylamino acid racemase DNA-containing actinomycetous DNA library can be obtained by the above-mentioned method or the like.

The acylamino acid racemase DNA can be cloned from among the actinomycetous DNA library, for example by the method of Huynh et al. [DNA Cloning, a practical approach, 1, 49 (1985)] using the phage vector λgt11 and an acylamino acid racemase antibody or the colony hybridization or plaque hybridization method [Maniatis, T. et al., Molecular Cloning, Cold Spring Harbor Laboratory, (1982)] using, as a probe, an oligonucleotide chemically synthesized based on the amino acid sequence of Amycolatopsis sp. TS-1-60-derived acylamino acid racemase.

The thus-cloned acylamino acid racemase DNA can be subcloned, if necessary or where appropriate, into a plasmid, for example pBR322, pUC12, pUC13, pUC18, pUC19, pUC118 or pUC119.

The thus-obtained DNA is sequenced, for example by the Maxam-Gilbert method [Maxam, A. M. and Gilbert, W., Proc. Natl. Acad. Sci. U.S.A., 74, 560 (1977)] or the dideoxy method [Messing, J. et al., Nucl. Acids Res., 9, 309 (1981)] or the deaza method [Mizusawa, S. et al., Nucl. Acids Res., 14, 1319 (1986)] and the base sequence is compared with the known amino acid sequence to thereby confirm the existence of the acylamino acid racemase DNA. In cases where all the region encoding acylamino acid racemase is not covered, colony hybridization is carried out using the DNA fragment as a probe for recloning of the acylamino acid racemase to thereby fill up the missing region.

In the above manner, a DNA coding for acylamino acid racemase is obtained.

As a typical example of the DNA according to the invention which encodes acylamino acid racemase, there may be mentioned the acylamino acid racemase-encoding DNA obtained in Example 1 to be described later herein. Its restriction enzyme cleavage map is shown in FIG. 2.

The DNA encoding acylamino acid racemase as cloned in the above manner can be used either as such where appropriate or, if desired, after restriction enzyme digestion or site-directed mutagenesis [Methods in Enzymology, 100, 468 (1983)], for instance, for improving the plasmid.

The above-mentioned cloned DNA encoding N-acylamino acid racemase can be expressed in large amounts in *Escherichia coli*, for instance, using a promoter such as the lac promoter, tac promoter [de Boyer, H. A., Camstock, L. J., Vasser, M., Proc. Natl. Acad. Sci. U.S.A., 80, 21 (1980)], T7 promoter [Tabor, S., Richardson, C. C., Proc. Natl. Acad. Sci. U.S.A., 82, 1074 (1985)].

A microorganism (e.g. actinomycete, *Escherichia coli*, yeast) transformed with the above-mentioned cloned DNA is cultivated, whereby acylamino acid racemase is produced in the culture medium and can be recovered therefrom.

It is also possible to improve some property or properties of acylamino acid racemase itself (e.g. enzyme activity, stability) by the above-mentioned methods.

As the host to be used for the expression, there may be mentioned *Streptomyces lividans* TK64 and *Escherichia coli* HB101, for instance. Also usable are other actinomycetes, other *Escherichia coli* strains, *Bacillus subtilis* and, further, yeasts.

The transformation of actinomycetes is per se known and is carried out by the method of Hopwood, D. A. et al. (as described in Genetic Manipulation of Streptomyces, A Laboratory Manual).

The transformation of *Escherichia coli* is also known and can be performed by the calcium chloride method described in Maniatis, T. et al., Molecular Cloning, Cold Spring Harbor Laboratory, page 239, 1982, or by the calcium chloride/rubidium chloride method.

As a typical example of such transformant according to the invention, there may be mentioned *Escherichia coli* ER-4 (IFO 15083; FERM BP-3091).

It is possible, of course, to produce various transformants with ease in the same manner as described herein by appropriately selecting receptor organisms.

The thus-obtained transformants are cultivated by a per se known method. In cultivating actinomycetes, the seed medium is as follows: 3% glycerol, 0.5% polypeptone, 0.3% meat extract, 0.05% N-acetyl-DL-methionine, pH 7.2; and the production medium is as follows: 1.7% pancreatin-treated casein, 0.3% papain-treated defatted soybean flour, 0.5% sodium chloride, 0.25% dipotassium hydrogen phosphate, 1% glucose, 0.05% N-acetyl-DL-methionine, pH 7.0. The cultivation is carried out generally at 15°–40° C., preferably at 24°–30° C., for 10–96 hours, preferably for 24–72 hours. If necessary, aeration and/or agitation may be made. In cultivating *Escherichia coli*, LB medium (1% polypeptone, 0.5% yeast extract, 0.5% sodium chloride) is used as the medium. The cultivation is carried out generally at 15°–40° C., preferably at 24°–37° C., for 10–96 hours, preferably for 24–48 hours. If necessary, aeration and/or agitation may be made.

After completion of the cultivation, the cells and the supernatant are separated from each other. The acylamino acid racemase remaining in the cells is extracted by a cell disruption method commonly used in this field of art, for example sonication, disruption by means of a French press, mechanical disruption by grinding or the like, or treatment with lysozyme. The acylamino acid racemase contained in the thus-obtained extract is purified by subjecting said extract to a usual method of protein purification, for example salting out, isoelectric precipitation, gel filtration, ionexchange chromatography, hydrophobic chromatography, or high-performance liquid chromatography, whereby the desired acylamino acid racemase can be obtained.

The activity of the acylamino acid racemase obtained in the above manner is measured by the known method (Japanese Kokai Tokkyo Koho JP 01-137973). Thus, 50–100 µl of an enzyme solution is added to a reaction medium comprising 25 mM N-acetyl-DL-methionine, 2 mM cobalt chloride, 2 U L-acylase and 50 mM Tris-hydrochloride buffer (pH 7.5) and the reaction is allowed to occur at 30° C. for 5 minutes and then stopped by boiling for 3 minutes. One unit (U) of enzyme is defined as an amount of enzyme causing formation of 1 µmol of L-methionine per minute.

The abbreviations and symbols used herein for bases, amino acids, etc. are those recommended by the IUPAC-IUB Commission on Biochemical Nomenclature or commonly used in the relevant fields. Examples are shown below. As for those amino acids which may occur in optical isomer forms, the abbreviations used, unless otherwise specified, denote the L isomers.

| DNA | Deoxyribonucleic acid |
| --- | --- |
| A | Adenine |
| C | Cytosine |
| G | Guanine |
| T | Thymine |
| Ala | Alanine |
| Arg | Arginine |
| Asn | Asparagine |
| Asp | Aspartic acid |
| Cys | Cysteine |
| Gln | Glutamine |
| Glu | Glutamic acid |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

EXAMPLES

The following examples are further illustrative of the present invention but are by no means limitative of the scope thereof.

Example 1

Isolation of chromosomal DNA of Amycolatopsis sp. TS-1-60.

Amycolatopsis sp. TS-1-60 was shake-cultured in a 200-ml erlenmeyer flask containing 20 ml of Trypticase Soy Broth (Becton Dickinson) at 28° C. for 42 hours. The wet cells (4 g) obtained were suspended in 20 ml of buffer A [0.3M sucrose, 25 mM EDTA, 25 mM Tris-HCl buffer (pH 8)] and, after addition of egg white lysozyme to a concentration of 2 mg/ml, the suspension was shaken gently at 37° C. for 1 hour. Then, 8 ml of 2% SDS was added to the suspension, followed by two or three gentle swirlings. Thereto were added 5 ml of chloroform and 5 ml of buffer A-saturated phenol, and the whole mixture was centrifuged (3,000 rpm, 20 minutes) for DNA extraction. After three repetitions of this phenol extraction, one tenth volume of 3M potassium acetate and 2 volumes of ice-cooled ethanol were added to the DNA solution for DNA precipitation. The precipitate DNA was collected by centrifugation, washed with 70% ethanol, dried in vacuo, and stored.

Example 2

Cloning of an acylamino acid racemase-encoding gene (A) Preparation of a gene library a) Partial digestion with the restriction enzyme HaeIII The chromosomal DNA of Amycolatopsis sp. TS-1-60 as isolated in Example 1 was partially digested with the restriction enzyme HaeIII (Takara Shuzo). Thus, the reaction was allowed to proceed at 37° C. for 2 minutes in a total volume of 50 μl of a reaction system composed of 10 mM Tris-HCl buffer (pH 7.5), 7 mM magnesium chloride, 60 mM sodium chloride, 7 mM 2-mercaptoethanol, 5 μg of the donor DNA and 10 units of HaeIII. The reaction mixture was deproteinized by phenol-chloroform treatment and the digest DNA was recovered by addition of 2 volumes of ethanol.

b) Methylase reaction

The DNA fragment partially digested with HaeIII was methylated on the adenosine moiety in the EcoRI site. Thus, 5 μg of the partial digest DNA fragment was treated in a total volume of 20 μl of a reaction medium composed of 100 mM Tris-HCl buffer (pH 8), 2 mM dithiothreitol, 10 mM EDTA, 80 μM S-adenosylmethionine and 40 units of methylase (Takara Shuzo) at 37° C. for 60 minutes. The methylated DNA fragment was recovered in the same manner as mentioned above.

c) Linker ligation

An EcoRI linker was joined to the terminus of the methylated DNA fragment. The EcoRI linker used was d (pGGAATTCC) (Takara Shuzo). For the linker joining, a ligation kit (Takara Shuzo) was used. The reaction was carried out at 16° C. for 16 hours using a total of 20 μl of a mixture composed of 5 μg of the DNA, 2 μl (2 μg) of the EcoRI linker, 16 μl of solution A and 2 μl of solution B. The reaction mixture was treated with chloroform/phenol and the product DNA was then recovered by ethanol precipitation followed by drying.

d) Digestion with the restriction enzyme EcoRI

5 μg of the DNA fragment obtained in c) was digested with the restriction enzyme EcoRI at 37° C. for 3 hours. The resultant DNA fragments were electrophoresed and DNA fragments 1 to 3 kbp in size were recovered, subjected to phenol-chloroform treatment and ethanol precipitation and, after drying in vacuo, dissolved in 20 μl of TNE buffer (10 mM Tris-HCl, 1 mM EDTA, 300 mM NaCl, pH 8.0).

e) Ligation with vector (λgt11) and packaging

λgt11 (Stratagene Cloning Systems, U.S.A.) was treated with EcoRI and with phosphatase and ligated with the DNA fragments (1–3 kbp) and the ligation reaction mixture was packaged using Gigapack gold (Stratagene Cloning Systems, U.S.A.).

(B) Preparation of probes

Acylamino acid racemase (purified protein, 4 mg) produced by Amycolatopsis sp. TS-1-60 was cleaved into several peptides by treatment with lysyl endopeptidase. The peptides were purified by reversed-phase chromatography and the amino acid sequence of a peptide named peak 2 was determined. The sequence was Lys Leu Gly Ala Val Gln Ile Val Asn Ile Lys Pro Gly Arg Val Gly Gly Tyr (SEQ ID NO. 2). The following oligonucleotide deduced from the underlined peptide portion was synthesized: 5'-GAGATCCTR$^4$AACATCAAGCC-3' (R$^4$ being G or C) (SEQ ID NO. 3). This oligonucleotide was labeled with $^{32}$P at the 5' end by the conventional method for its use as a probe.

(c) Preparation of an antibody against acylamino acid racemase

Rabbits were challenged with about 1 mg of the purified acylamino acid racemase protein obtained from Amycolatopsis sp. TS-1-60 in four divided doses (400, 200, 200 and 200 μg). As a result, a polyclonal antibody-containing serum was obtained which had an antibody titer of 16 as determined by the Ouchterlony method.

(D) Screening by immunoassay

*Escherichia coli* Y1090 was transfected with the λgt11 DNA library derived from Amycolatopsis sp. TS-1-60 and 13 positive plaques were obtained from among about 200,000 plaques. They were purified and proliferated, the DNAs were extracted therefrom and cleaved with EcoRI, and the digests were subjected to electrophoresis. The DNA fragments separated by electrophoresis were labeled with $^{32}$P and subjected to Southern hybridization using the probe mentioned above. Of the 13 recombinant phages, two phages, λ-8 and λ-9, hybridized with the probe. Then, using part of the EcoRI fragments of λ-9, a probe of about 600 bp was prepared. Using this probe, plaque hybridization was again performed with about 50,000 plaques obtained from the λgt11 DNA library. As a result, λ-44 was obtained and, upon minute investigation, this was found to contain the whole DNA encoding acylamino acid racemase.

Example 3

Base sequence determination (sequencing)

An EcoRI fragment (1.2 kbp) isolated from λ-44 was inserted into the *Escherichia coli* phages M13mp8 and M13mp9 by the method of Messing et al. [Nucl. Acids Res., 9, 309 (1981)] and sequenced by the deaza method [Mizusawa, S. et al., Nucl. Acids Res., 14, 1319 (1986)]. The results is shown in FIG. 1. Part of the amino acid sequence deduced from this base sequence was in agreement with that part of the amino acid sequence of acylamino acid racemase purified rom Amycolatopsis sp. TS-1-60. It was thus found that λ-44 contained a gene encoding acylamino acid racemase.

Example 4

Production of acylamino acid racemase using a transformant of an actinomycete

*Streptomyces lividans* TK64/pRA32 was used. This strain was produced by extracting the acylamino acid racemase gene from the whole DNA of Amycolatopsis sp. TS-1-60, inserting said gene into pIJ702, a plasmid for use in actinomycetes, and transforming *Streptomyces lividans* TK64 with the resulting recombinant plasmid. Said strain was cultured on a yeast extract-malt extract agar slant medium (ISP2 medium) at 28° C. for 7 days. One loopful of the spores thus formed was inoculated into 20 ml of sterilized seed medium (3% glycerol, 0.5% polypeptone, 0.3% meat extract, 0.05% N-acetyl-DL-methionine, pH 7.2) in each 200-ml erlenmeyer flask and cultured on a rotary shaker (200 rpm) at 28° C. for 48 hours. The culture was distributed in 8-ml portions into 15-ml vials and stored frozen at −80° C. (frozen stock culture). The first seed was prepared by inoculating the same seed medium as mentioned above with 1 ml of the frozen stock culture and conducting cultivation under the same conditions as mentioned above. The second seed was prepared by inoculating a sterilized 500-ml portion of the seed medium in each 2-liter Sakaguchi flask with 20 ml of the first seed culture and carrying out cultivation on a reciprocal shaker (78 spm) at 28° C. for 72 hours. For enzyme production, 100 liters of a production medium (1.7% pancreatin-treated casein, 0.3% papin-treated defatted soybean flour, 0.5% sodium chloride, 0.25% dipotassium hydrogen phosphate, 1% glucose, 0.05% N-acetyl-DL-methionine, pH 7.0) placed and sterilized in each 200-liter fermentor was inoculated with 4 liters of the second seed culture and cultivation was performed at 28° C. for 42 hours with aeration (80 vvm) and agitation (160 rpm). As a control, the DNA donor Amycolatopsis sp. TS-1-60 was cultivated in the same manner. Comparison from the enzyme production viewpoint revealed that the transformat showed higher productivity.

Example 5

Figure 3:
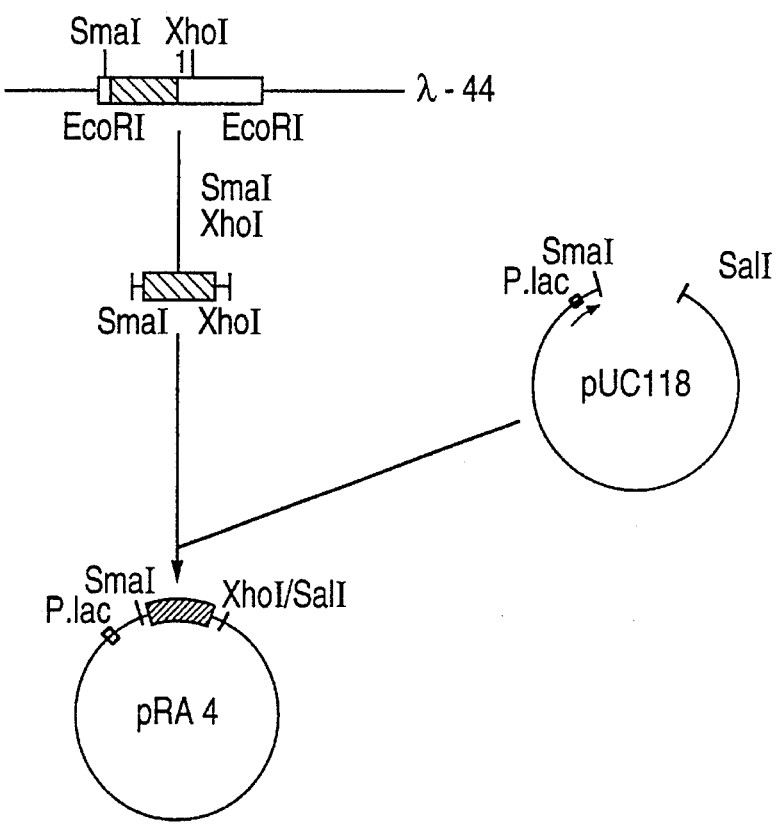
FIG. 3 shows a process for preparing the plasmid pRA4.

Expression of the acylamino acid racemase gene in *Escherichia coli* using the lac promoter A SmaI-XhoI fragment containing the structural gene for acylamino acid racemase was separated from the recombinant phage λ-44. This fragment was inserted into the *Escherichia coli* plasmid pUC118 at the multicloning site (SmaI-SalI site) thereof in the same orientation as that of the lac promoter to give a plasmid, pRA4 (FIG. 3). This plasmid pRA4 was used to transform *Escherichia coli* JM105.

The resultant transformant strain ER-4 (IFO 15083; FERM BP-3091) was picked up with a bamboo stick for inoculation of 4 ml of LB medium (1% polypeptone, 0.5% yeast extract, 0.5% sodium chloride) containing ampicillin (50 μg/ml) and shake culture was carried out at 37° C. for 16 hours. A 0.3-ml portion of the culture was inoculated into 30 ml of LB medium containing ampicillin (50 μg/ml) and shake culture was performed at 37° C. for 3 hours. Then, 3 ml of 0.1M IPTG (isopropyl β-D-thiogalactopyranoside) was added (final concentration 1 mM) and cultivation was continued further for 4 hours. Cells were collected (3,000 rpm, 10 minutes), suspended in 5 ml of Tris-hydrochloride buffer (50 mM, pH 7.5) and sonicated (4 minutes). The resultant cell disruption product was subjected to centrifugation (15,000 rpm, 10 minutes) and the supernatant was subjected to acylamino acid racemase activity determination by the known method. Acylamino acid racemase activity, which was not observed with the host *Escherichia coli* JM105, could be confirmed with the transformant ER-4. The enzyme productivity was 64 U/liter (medium) and about 3 times as compared with the DNA donor Amycolatopsis sp. TS-1-60.

Example 6

Figure 4:
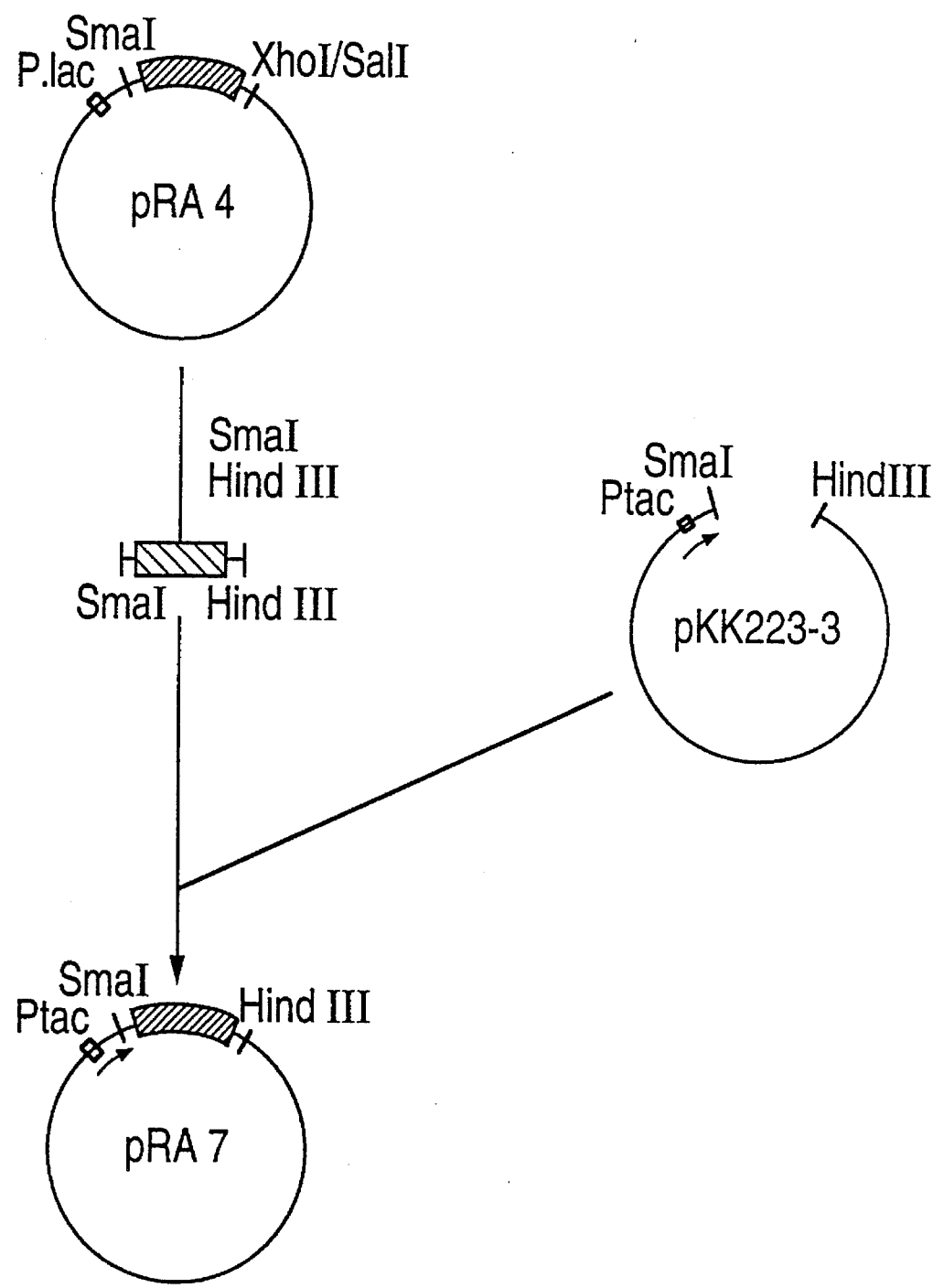
FIG. 4 shows a process for preparing the plasmid pRA7.

Expression of the acylamino acid racemase gene in *Escherichia coli* using the tac promoter A SmaI-HindIII fragment containing the structural gene for acylamino acid racemase was excised from the lac expression plasmid pRA4 of Example 5. This fragment was inserted into the tac promoter-containing expression plasmid vector pKK223-3 [Brosius, J and Holly, A., Proc. Natl. Acad. Sci. U.S.A., 81, 6929 (1984)] at the SmaI-HindIII site thereof to give a plasmid, pRA7 (FIG. 4). This plasmid pRA7 was used to transform *Escherichia coli* JM105.

The resultant transformant ER7 was cultivated by the method described in Example 5 and the acylamino acid racemase activity was measured by the known method, whereby said enzyme activity was observed. The enzyme productivity was 34 U/liter (medium), which was about 1.5 times higher than that found with the DNA donor Amycolatopsis sp. TS-1-60.

Example 7

Initiation codon conversion from GTG to ATG

Figure 5:
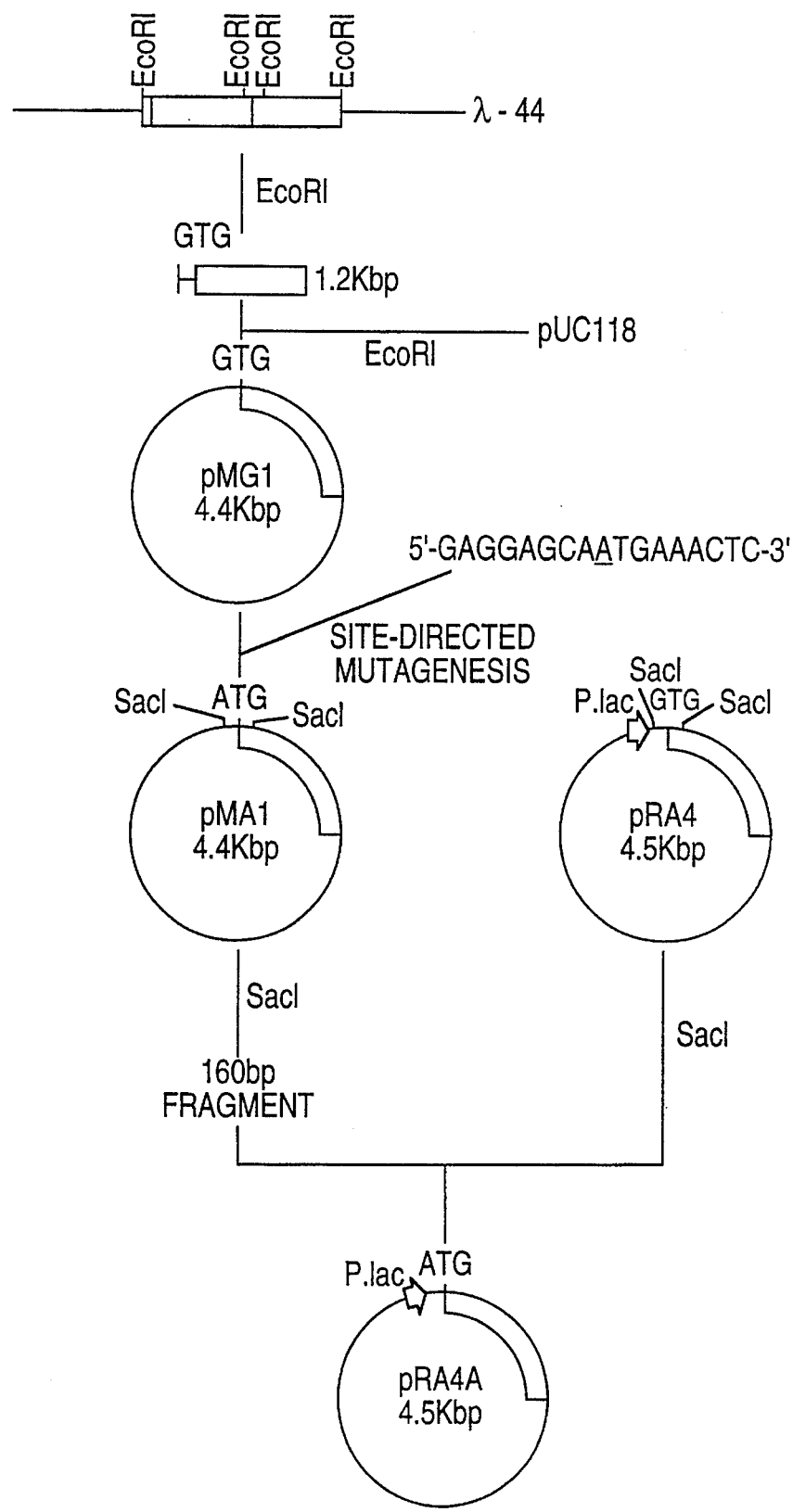
FIG. 5 shows a process for preparing the plasmid pRA4A.
Figure 6:
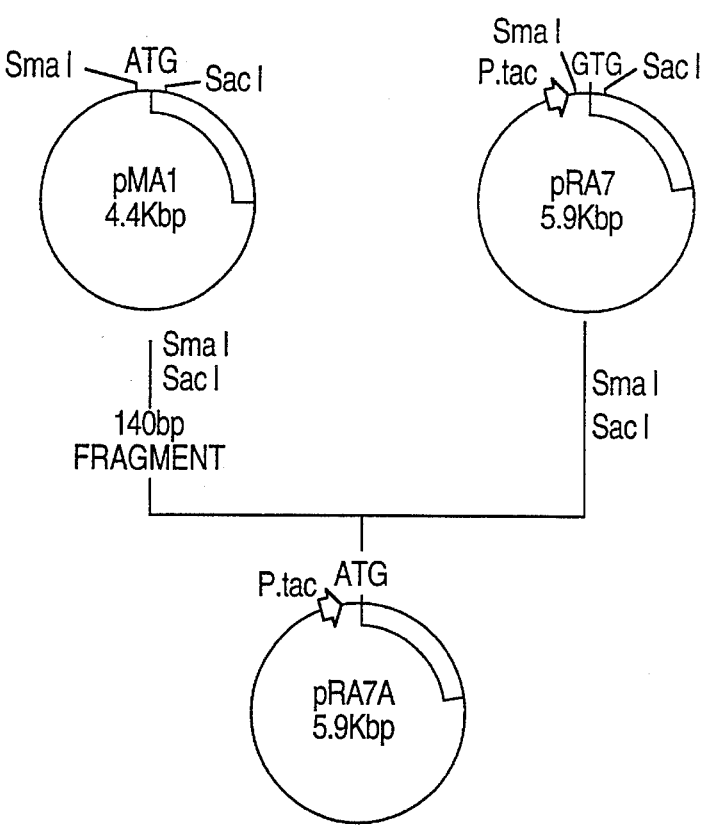
FIG. 6 shows a process for producing the plasmid pRA7A.

An initiation codon-containing EcoRI fragment was separated and recovered from the recombinant phage λ-44 and inserted into the plasmid vector pUC118 at the EcoRI site thereof. The resultant recombinant plasmid was used to transform *Escherichia coli* MV1184 and a single-stranded DNA was prepared from a transformant obtained by the method of Vieira et al. [Methods in Enzymology, 100, 3 (1987)]. Site-directed mutagenesis was performed using a mutation point-containing synthetic oligonucleotide 5'-GAGGAGCAATGAAACTC-3'(SEQ ID NO. 4) in in vitro Mutagenesis System, version 2.0 (Amersham). A mutation point-containing SacI fragment was separated and recovered from the resultant mutant plasmid pMA1 and joined to the expression plasmid pRA4 treated in advance with SacI, to give a lac promoter expression plasmid, pRA4A, in which the initiation codon had been converted to ATG (FIG. 5). Similarly, a mutation point-containing SmaI/SacI fragment was separated and recovered from the mutant plasmid pMA1 and joined to the expression plasmid pRA7 treated in advance with SmaI/SacI, to give a tac promoter expression plasmid, pRA7A, in which the initiation codon had been converted to ATG (FIG. 6). These mutant expression plasmids were used to transform *Escherichia coli* JM105, respectively giving transformants, ER4A (JM105/pRA4A) and ER7A (JM105/pRA7A; IFO 15131, FERM BP-3272). These transformants were cultivated by the method of Example 5 for 9 hours following addition of IPTG and acylamino acid racemase activity measurements were made by the per se known method. The enzyme productivities were 740 U/liter (medium) for the strain ER4A and 198 U/liter (medium) for the strain ER7A, being about 37 times and about 10 times higher, respectively, as compared with the DNA donor Amycolatopsis sp. TS-1-60.

Example 8

Expression of acylamino acid racemase gene in *Escherichia coli* using T7 promoter For subcloning the acylamino acid racemase gene in the T7 expression plasmid pET-3c [Gene, 56, 125 (1987)] at the NdeI/BamHI site thereof, an NdeI site (CATATG) was introduced into the initiation codon region and a BglII site (AGATCT) into the termination codon region using the technique of site-directed mutagenesis.

A) NdeI site introduction

Figure 7:
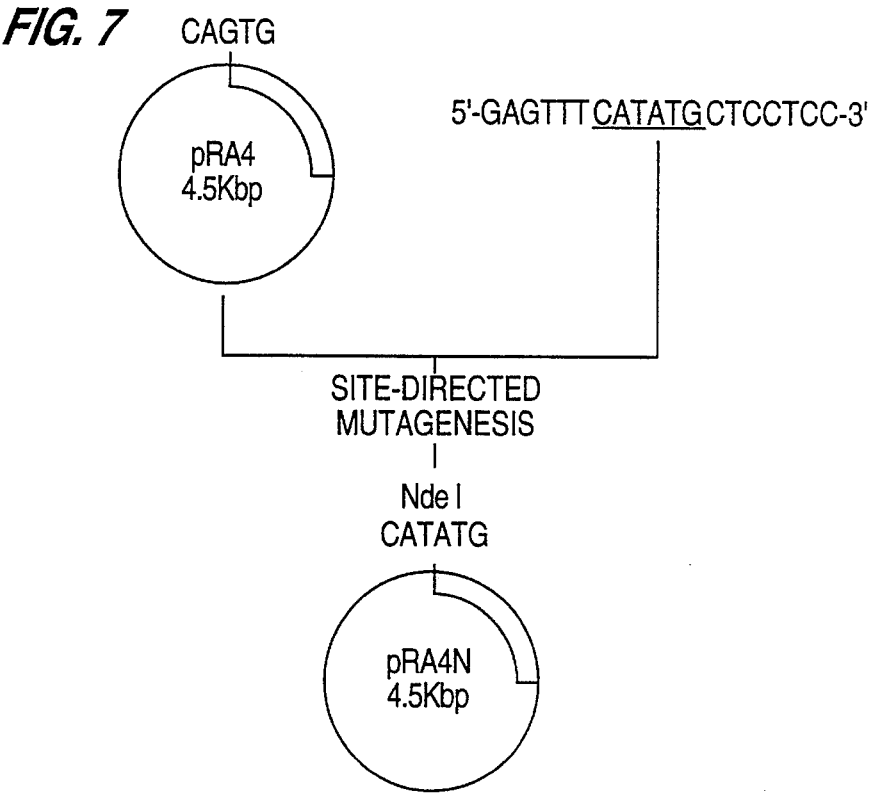
FIG. 7 shows a process for producing plasmid pRA4N.

*Escherichia coli* MV1184 was transformed with the expression plasmid pRA4 and a single-stranded DNA was prepared from one of the thus-obtained transformants using the method of Vieira et al. Using this single-stranded DNA and an NdeI site (CATATG)-containing synthetic oligonucleotide (5'-GAGTTTCATATGCTCCTCC-3') (SEQ ID NO. 5), site-directed mutagenesis [in, vitro Mutagenesis System, version 2.0 (Amersham)] was carried out to give a plasmid, pRA4N, having an NdeI site in the initiation codon region (FIG. 7).

B) BglII site introduction

Figure 8:
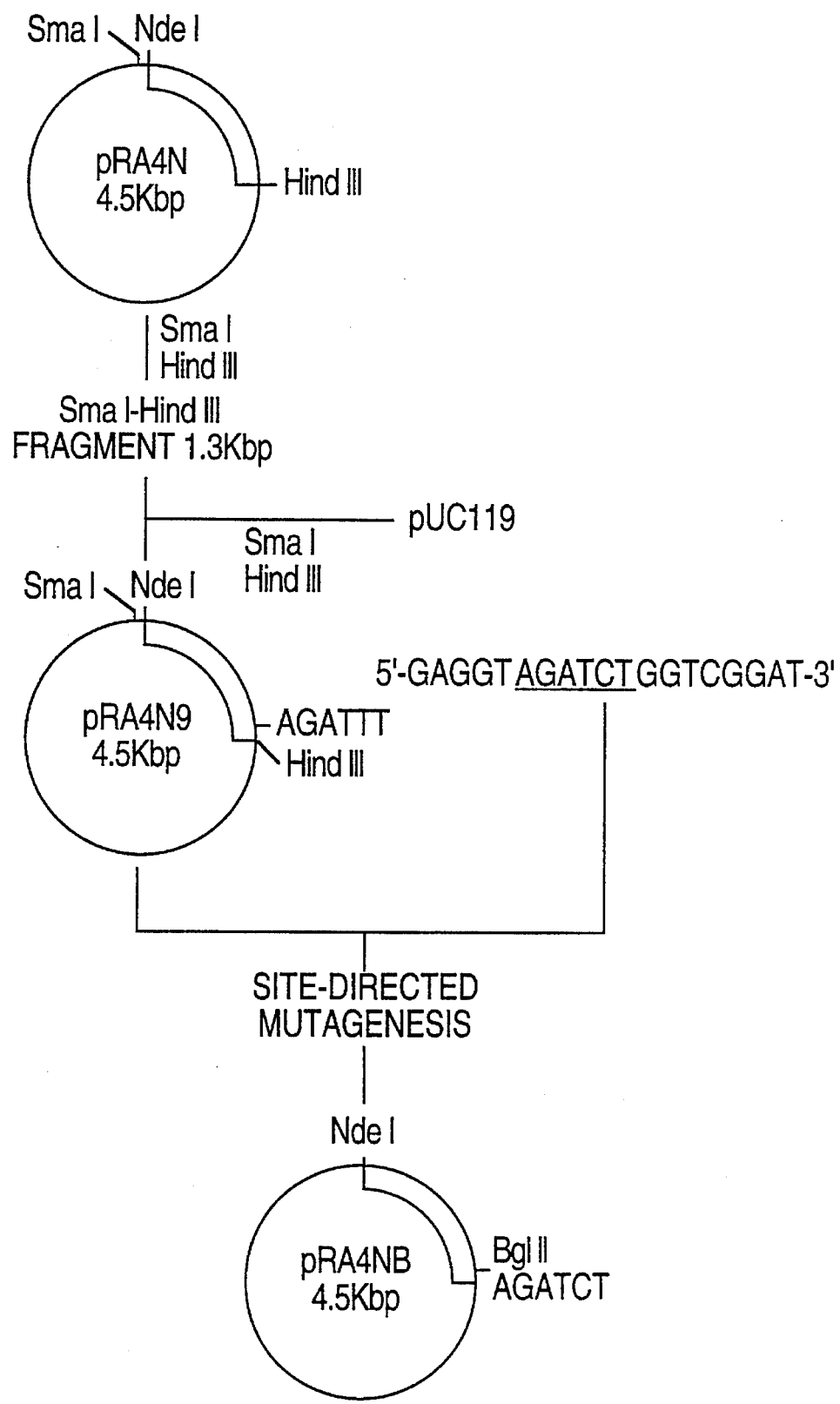
FIG. 8 shows a process for producing plasmid pRA4NB.

An NdeI site-containing SmaI/HindIII fragment was separated from the plasmid pRA4N and joined to the plasmid pUC119 treated in advance with SmaI and HindIII. The resultant recombinant plasmid was used to transform *Escherichia coli* MV1184. A single-stranded DNA was prepared from one of the thus-obtained transformants by the method of Vieira et al. Using this single-stranded DNA and a BglII site (AGATCT)-containing synthetic oligonucleotide (5'-GAGGTAGATCTGGTCGGAT-3') (SEQ ID NO. 6), site-directed mutagenesis was performed in the same manner as in A) to give a plasmid, pRA4NB, having a BglII site in the termination codon region (FIG. 8).

C) Expression

Figure 9:
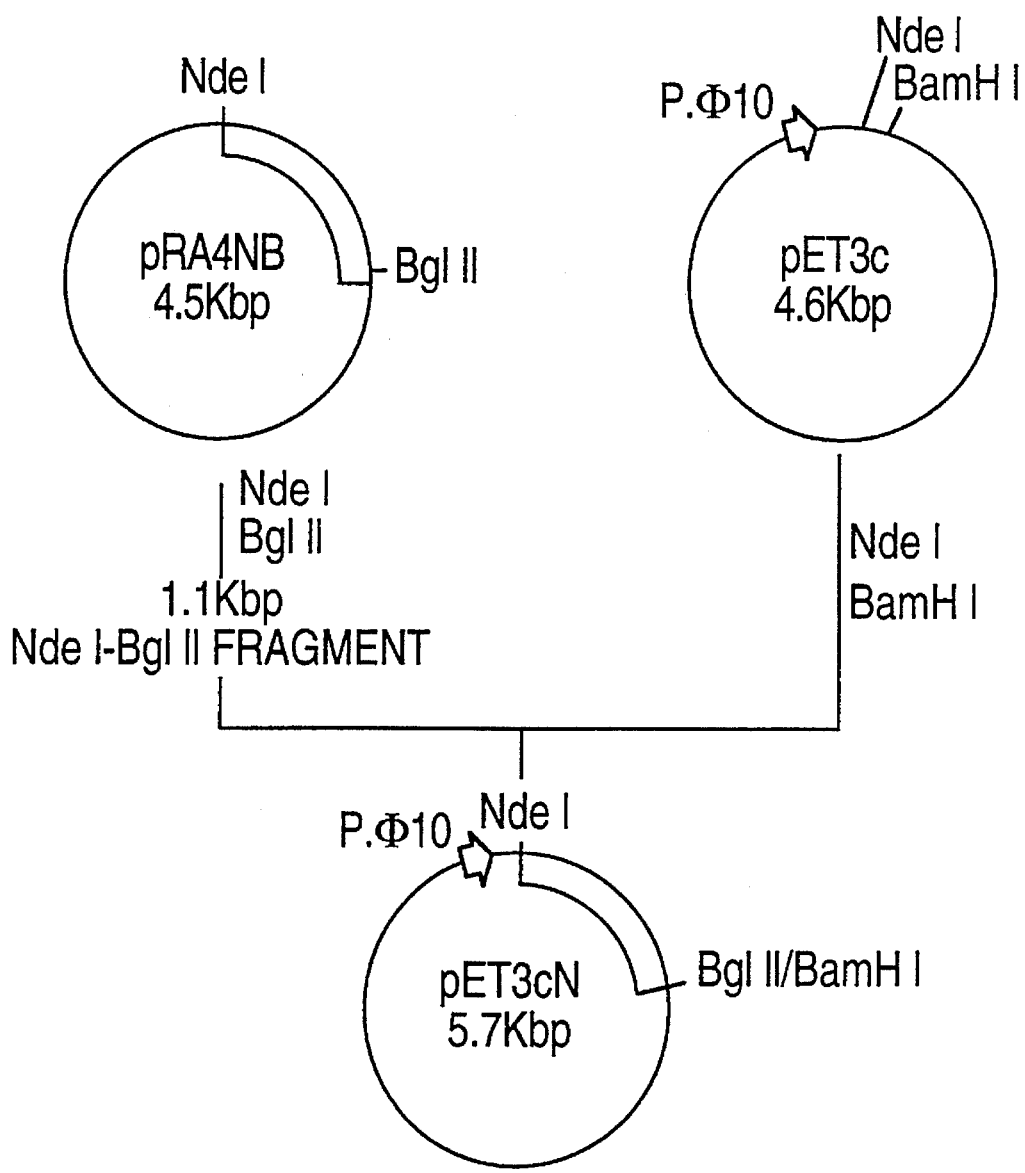
FIG. 9 shows a process for producing plasmid pET-3cN.

An NdeI/BglII fragment containing the enzyme gene in question was separated and recovered from the plasmid pRA4NB and inserted into the plasmid pET-3c between the NdeI site and BamHI site thereof to give an acylamino acid racamase expression plasmid, pET-3cN (FIG. 9). This plasmid was used to transform *Escherichia coli* MM294 (DE3), whereby a transformant, MR-1 (IFO 15132, FERM BP-3273), was obtained. This transformant was cultivated by the method described in Example 7 and the acylamino acid racamase activity as measured by the per se known method. The enzyme productivity was 1,795 U/liter (medium). This was about 90 times higher as compared with the DNA donor Amycolatopsis sp. TS-1-60.

D) Tank culture (20 liters) of transformant MR-1

LB medium containing ampicillin (50 μg/ml) was distributed in 400-ml portions into one-liter erlenmeyer flasks and sterilized. The medium in each flask was inoculated with one loopful of cells of the strain MR-1. Shake culture (250 rpm) was carried out at 37° C. for 20 hours. One liter of the culture fluid thus obtained was inoculated into 20 liters of M9 medium [Maniatis, T. et al., Molecular Cloning, Cold Spring Harbor Laboratory (1982)] supplemented with polypeptone (1.53%) and cultured at 28° C. for 34 hours with aeration (100 vvm) and stirring (450 rpm). At 8 hours after initiation of cultivation, IPTG was added to a final concentration of 0.01 mM and cultivation was continued with continuous addition (150 ml/hour) of a mixed solution of 8% glucose and 2% polypeptone. After completion of the cultivation, the culture was centrifuged (1,000 rpm, 20 minutes) to give 1,320 g of wet cells. The acylamino acid racamase activity was measured by the per se known method. The enzyme productivity was 22,300 U/liter (medium). This was about 1,100 times higher as compared with the DNA donor Amycolatopsis sp. TS-1-60.

Example 9

Enzyme purification for *Escherichia coli* transformant

LB medium containing ampicillin (50 μg/ml) was distributed in 40-ml portions into 200-ml erlenmeyer flasks and sterilized. The medium in each flask was inoculated with one loopful of cells of the strain ER4A and shake culture (300 rpm) was conducted at 37° C. for 16 hours. The culture fluid thus obtained was transferred in 4-ml portions into one-liter erlenmeyer flasks each containing 400 ml of sterilized LB medium and shake culture (250 rpm) was carried out at 30° C. for 30 hours. At about 6 hours after initiation of cultivation, 4 ml of IPTG (0.1M) was added to each flask (final concentration 1 mM). Eight liters of the culture fluid was centrifuged (10,000 rpm, 20 minutes) to give 141 g of wet cells.

These cells were suspended in Tris-hydrochloride buffer (50 mM, pH 7.5) to make 500 ml and then disrupted by sonication (5 minutes×3). The cell disruption product fluid was made 1 liter by addition of the same buffer and magnesium sulfate (final concentration 10 mM), heat-treated (60° C., 30 minutes) and then centrifuged (10,000 rpm, 20 minutes) to give 940 ml of a supernatant. To this supernatant was added 107.2 g (for 20% saturation) of ammonium sulfate. The resultant solution was allowed to stand at 0° C. for 2 hours and then centrifuged (10,000 rpm, 30 minutes), and the supernatant thus obtained was applied to a BUTYL-Toyopearl column (BUTYL-Toyopearl 650M, Tosoh, 4.5× 30 cm) equilibrated in advance with Tris-hydrochloride buffer containing 20% saturated ammonium sulfate. The column was washed with 2 liters of the same buffer containing 20% saturated ammonium sulfate, followed by elution with the same buffer while the ammonium sulfate solution was varied from 20% saturation to 0% saturation. The eluate was fractionated in 20-ml portions. The acylamino acid racamase activity was observed in the 34th to 50th fractions. The active fractions were combined, dialyzed against the same buffer and applied to a DEAE-Toyopearl column (DEAE-Toyopearl 650M, Tosoh, 4.1×16 cm) equilibrated in advance with the same buffer. The column was washed with 1 liter of the same buffer. Elution was carried out with 1 liter of the same buffer containing sodium chloride whose concentration was varied from 0 to 0.5M. The eluate was fractionated in 10-ml portions. The acylamino acid racamase activity was observed in the 48th to 53rd fractions. The above procedure gave 1,570 U of acylamino acid racamase showing a substantially single band in SDS-polyacrylamide gel electrophoresis. The results of purification of this enzyme from the transformant ER4A are shown below.

| Step | Total protein (mg) | Total activity (units) | Specific activity (units/mg) | Purity (fold) | Yield (%) |
| --- | --- | --- | --- | --- | --- |
| Cell disruption | 18000 | 3180 | 0.17 | 1.0 | 100 |
| Heat treatment | 7123 | 3256 | 0.46 | 2.7 | 100 |
| BUTYL-Toyopearl | 249 | 1620 | 6.50 | 38.2 | 51 |
| DEAE-Toyopearl | 198 | 1573 | 13.5 | 79.4 | 49 |

---

What is claimed is:

1. An isolated and purified DNA sequence encoding an α-N-acylamino acid racemase consisting of nucleotides 62 to 1165 of SEQ ID No. 1.

2. An isolated and purified DNA sequence encoding an α-N-acylamino acid racemase consisting of nucleotides 1 to 1400 of SEQ ID NO: 1.

3. A vector comprising the DNA sequence of claim 1.

4. A vector comprising the DNA sequence of claim 2.

5. A plasmid comprising the DNA sequence of claim 1.

6. A plasmid comprising the DNA sequence of claim 2.

7. A transformat containing the vector of claim 3.

8. A transformant containing the vector of claim 4.

9. A method of using the DNA sequence of claim 1, which comprises cultivating a transformant containing a plasmid comprising the DNA sequence of claim 1 in a medium under conditions to produce the α-N-acylamino acid racemase encoded by the DNA sequence, and recovering the racemase from the culture.

10. A method of using the DNA sequence of claim 2, which comprises cultivating a transformant containing a plasmid comprising the DNA sequence of claim 2 in a medium under conditions to produce the α-N-acylamino acid racemase encoded by the DNA sequence, and recovering the racemase from the culture.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1400 base pairs
( B ) TYPE: nucleic acid
( C ) STRANDEDNESS: double
( D ) TOPOLOGY: linear ( i i ) MOLECULE TYPE:

(iii) HYPOTHETICAL:

(iv) ANTI-SENSE:

(v) FRAGMENT TYPE:

(vi) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:
  (A) LIBRARY:
  (B) CLONE:

(viii) POSITION IN GENOME:
  (A) CHROMOSOME/SEGMENT:
  (B) MAP POSITION:
  (C) UNITS:

(ix) FEATURE:
  (A) NAME/KEY:
  (B) LOCATION:
  (C) IDENTIFICATION METHOD:
  (D) OTHER INFORMATION:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO:1:

```
GAATTCCCCG GGTGACCGGC TTCGACCGAG CCGGCTTTTA CGTGATCTCC AAGGAGGAGC        60

A GTG AAA CTC AGC GGT GTG GAA CTG CGC CGG GTG CAG ATG CCG CTC GTC      109
  Met Lys Leu Ser Gly Val Glu Leu Arg Arg Val Gln Met Pro Leu Val
  1           5                   10                  15

GCC CCG TTC CGG ACT TCG TTC GGC ACC CAG TCG GTC CGC GAG CTC TTG        157
Ala Pro Phe Arg Thr Ser Phe Gly Thr Gln Ser Val Arg Glu Leu Leu
            20                  25                  30

CTG CTG CGC GCG GTC ACG CCG GCC GGC GAG GGC TGG GGC GAA TGC GTG        205
Leu Leu Arg Ala Val Thr Pro Ala Gly Glu Gly Trp Gly Glu Cys Val
        35                  40                  45

ACG ATG GCC GGT CCG CTG TAC TCG TCG GAG TAC AAC GAC GGC GCG GAA        253
Thr Met Ala Gly Pro Leu Tyr Ser Ser Glu Tyr Asn Asp Gly Ala Glu
    50                  55                  60

CAC GTG CTG CGG CAC TAC TTG ATC CCG GCG CTG CTG GCC GCG GAA GAC        301
His Val Leu Arg His Tyr Leu Ile Pro Ala Leu Leu Ala Ala Glu Asp
65                  70                  75                  80

ATC ACC GCG GCG AAG GTG ACG CCG CTG CTG GCC AAG TTC AAG GGC CAC        349
Ile Thr Ala Ala Lys Val Thr Pro Leu Leu Ala Lys Phe Lys Gly His
                85                  90                  95

CGG ATG GCC AAG GGC GCG CTG GAG ATG GCC GTG CTC GAC GCC GAA CTC        397
Arg Met Ala Lys Gly Ala Leu Glu Met Ala Val Leu Asp Ala Glu Leu
            100                 105                 110

CGC GCG CAC GAG AGG TCG TTC GCC GCC GAA CTC GGA TCG GTG CGC GAT        445
Arg Ala His Glu Arg Ser Phe Ala Ala Glu Leu Gly Ser Val Arg Asp
```

```
                        115                           120                           125
TCT  GTG  CCG  TGC  GGC  GTT  TCG  GTC  GGG  ATC  ATG  GAC  ACC  ATC  CCG  CAA                493
Ser  Val  Pro  Cys  Gly  Val  Ser  Val  Gly  Ile  Met  Asp  Thr  Ile  Pro  Gln
     130                      135                      140

CTG  CTC  GAC  GTC  GTG  GGC  GGA  TAC  CTC  GAC  GAG  GGT  TAC  GTG  CGG  ATC                541
Leu  Leu  Asp  Val  Val  Gly  Gly  Tyr  Leu  Asp  Glu  Gly  Tyr  Val  Arg  Ile
145                      150                      155                      160

AAG  CTG  AAG  ATC  GAA  CCC  GGC  TGG  GAC  GTC  GAG  CCG  GTG  CGC  GCG  GTC                589
Lys  Leu  Lys  Ile  Glu  Pro  Gly  Trp  Asp  Val  Glu  Pro  Val  Arg  Ala  Val
               165                      170                      175

CGC  GAG  CGC  TTC  GGC  GAC  GAC  GTG  CTG  CTG  CAG  GTC  GAC  GCG  AAC  ACC                637
Arg  Glu  Arg  Phe  Gly  Asp  Asp  Val  Leu  Leu  Gln  Val  Asp  Ala  Asn  Thr
               180                      185                      190

GCC  TAC  ACC  CTC  GGC  GAC  GCG  CCG  CAG  CTG  GCC  CGG  CTC  GAC  CCG  TTC                685
Ala  Tyr  Thr  Leu  Gly  Asp  Ala  Pro  Gln  Leu  Ala  Arg  Leu  Asp  Pro  Phe
          195                      200                      205

GGC  CTG  CTG  CTG  ATC  GAG  CAG  CCG  CTG  GAA  GAG  GAG  GAC  GTG  CTC  GGC                733
Gly  Leu  Leu  Leu  Ile  Glu  Gln  Pro  Leu  Glu  Glu  Glu  Asp  Val  Leu  Gly
     210                      215                      220

CAC  GCC  GAA  CTG  GCC  CGC  CGG  ATC  CAG  ACA  CCG  ATC  TGC  CTC  GAC  GAG                781
His  Ala  Glu  Leu  Ala  Arg  Arg  Ile  Gln  Thr  Pro  Ile  Cys  Leu  Asp  Glu
225                      230                      235                      240

TCG  ATC  GTG  TCG  GCG  CGC  GCG  GCG  GCG  GAC  GCC  ATC  AAG  CTG  GGC  GCG                829
Ser  Ile  Val  Ser  Ala  Arg  Ala  Ala  Ala  Asp  Ala  Ile  Lys  Leu  Gly  Ala
               245                      250                      255

GTC  CAA  ATC  GTG  AAC  ATC  AAA  CCG  GGC  CGC  GTC  GGC  GGG  TAC  CTG  GAA                877
Val  Gln  Ile  Val  Asn  Ile  Lys  Pro  Gly  Arg  Val  Gly  Gly  Tyr  Leu  Glu
               260                      265                      270

GCG  CGG  CGG  GTG  CAC  GAC  GTG  TGC  GCG  GCG  CAC  GGG  ATC  CCG  GTG  TGG                925
Ala  Arg  Arg  Val  His  Asp  Val  Cys  Ala  Ala  His  Gly  Ile  Pro  Val  Trp
          275                      280                      285

TGC  GGC  GGG  ATG  ATC  GAG  ACC  GGC  CTC  GGC  CGG  GCG  GCG  AAC  GTC  GCG                973
Cys  Gly  Gly  Met  Ile  Glu  Thr  Gly  Leu  Gly  Arg  Ala  Ala  Asn  Val  Ala
     290                      295                      300

CTG  GCC  TCG  CTG  CCG  AAC  TTC  ACC  CTG  CCC  GGC  GAC  ACC  TCG  GCG  TCG               1021
Leu  Ala  Ser  Leu  Pro  Asn  Phe  Thr  Leu  Pro  Gly  Asp  Thr  Ser  Ala  Ser
305                      310                      315                      320

GAC  CGG  TTC  TAC  AAA  ACC  GAC  ATC  ACC  GAG  CCG  TTC  GTG  CTC  TCC  GGC               1069
Asp  Arg  Phe  Tyr  Lys  Thr  Asp  Ile  Thr  Glu  Pro  Phe  Val  Leu  Ser  Gly
               325                      330                      335

GGC  CAC  CTC  CCG  GTG  CCG  ACC  GGA  CCG  GGC  CTC  GGC  GTG  GCG  CCG  ATT               1117
Gly  His  Leu  Pro  Val  Pro  Thr  Gly  Pro  Gly  Leu  Gly  Val  Ala  Pro  Ile
               340                      345                      350

CCG  GAG  CTG  CTG  GAC  GAG  GTG  ACC  ACG  GCA  AAG  GTG  TGG  ATC  GGT  TCG               1165
Pro  Glu  Leu  Leu  Asp  Glu  Val  Thr  Thr  Ala  Lys  Val  Trp  Ile  Gly  Ser
          355                      360                      365

TAGCCCGCTA  CGAATTCCGG  AGGTAGATTT  GGTCGGATCG  GACCAGCCGG  TCCGCACGAG               1225

GCCGGATCTA  CCTTCGGGGG  GTGCTGACAC  CGGTGCCGAG  CAAACCGCAC  ACGAGTCTGG              1285

GACGCGTCCT  CGAAGCTCTC  GGGGACGTGC  TCCTCGAGCC  GGTCGCCGTC  GGCGCGACAC              1345

GCGGCGGCAG  CTCGGCGGGG  TGGTGATTCA  CGACCCGCAC  GACGACGCGG  AATTC                   1400
```

( 2 ) INFORMATION FOR SEQ ID NO:2:

( i ) SEQUENCE CHARACTERISTICS:
        ( A ) LENGTH: 18 amino acid residues
        ( B ) TYPE: amino acid
        ( C ) STRANDEDNESS: single
        ( D ) TOPOLOGY: linear ( i i ) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:2:

```
Lys  Leu  Gly  Ala  Val  Gln  Ile  Val  Asn  Ile  Lys  Pro  Gly  Arg  Val
 1              5                        10                       15

Gly  Gly  Tyr
```

(2) INFORMATION FOR SEQ ID NO:3:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:3:

GAGATCCTSA ACATCAAGCC    20

( 2 ) INFORMATION FOR SEQ ID NO:4:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:

(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:4:

GAGGAGCAAT GAAACTC                                                  17

(2) INFORMATION FOR SEQ ID NO:5:

(i) SEQUENCE CHARACTERISTICS:
    (A) LENGTH: 19 bases
    (B) TYPE: nucleic acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:5:

GAGTTTCATA TGCTCCTCC                                                19

(2) INFORMATION FOR SEQ ID NO:6:

(i) SEQUENCE CHARACTERISTICS:
    (A) LENGTH: 19 bases
    (B) TYPE: nucleic acid
    (C) STRANDEDNESS: single (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:6:

GAGGTAGATC TGGTCGGAT                                                                 19